United States Patent [19]

Ajioka et al.

[11] Patent Number: 5,113,009

[45] Date of Patent: May 12, 1992

[54] PREPARATION AND ISOLATION OF MINERAL ACID SALT OF AN AMINO ACID METHYL ESTER

[75] Inventors: Masanobu Ajioka; Chojiro Higuchi; Takeshi Oura; Toshio Katoh; Akihiro Yamaguchi, all of Kanagawa, Japan

[73] Assignee: Mitsui Toatsu Chemicals, Incorporated

[21] Appl. No.: 457,076

[22] Filed: Dec. 26, 1989

[30] Foreign Application Priority Data

Dec. 27, 1988 [JP] Japan ............................ 63-327868

[51] Int. Cl.⁵ ............... C07C 103/32; C07C 101/02; C07C 101/26; C07C 101/30
[52] U.S. Cl. .................................. 560/40; 560/155; 560/169; 560/170; 560/171
[58] Field of Search ............... 560/40, 155, 169, 170, 560/171

[56] References Cited

U.S. PATENT DOCUMENTS

| | | | |
|---|---|---|---|
| 2,561,323 | 7/1951 | Waller et al. | 560/171 |
| 2,738,363 | 3/1956 | Gudefroi | 560/169 |
| 4,154,956 | 5/1979 | Veda et al. | 560/169 |

FOREIGN PATENT DOCUMENTS

| | | | |
|---|---|---|---|
| 727143 | 2/1966 | Canada | 560/155 |
| 32683 | 10/1970 | Japan | 560/155 |
| 41286 | 12/1971 | Japan | 560/170 |
| 165560 | 6/1989 | Japan . | |
| 290655 | 11/1989 | Japan | 560/155 |

OTHER PUBLICATIONS

Nippon Kagaku Zasshi (Nikkashi) 83 1151-4 (1962), Jun. 29, 1989, Chemical Abstracts Abstract.

Primary Examiner—J. E. Evans
Attorney, Agent, or Firm—Millen, White & Zelano

[57] ABSTRACT

A cyclical process for producing and isolating a mineral acid salt of an amino acid methyl ester in high purity and yield from the reaction solution produced by esterifying an amino acid with methanol in methanol in the presence of a mineral acid, by cooling the resulting reaction solution to precipitate crystals of the mineral acid salt; filtering the crystals;
  drying the isolated wet crystals or washing with another organic solvent; and recycling the filtrate for reuse in the esterification reaction.

13 Claims, No Drawings 500,113,009

PREPARATION AND ISOLATION OF MINERAL ACID SALT OF AN AMINO ACID METHYL ESTER

BACKGROUND OF THE INVENTION (i) Field of the Invention

The present invention relates to an improved process for the preparation of a mineral acid salt of an amino acid methyl ester and the isolation thereof from the esterification reaction solution in which it is produced. More specifically, it relates to a process for efficiently isolating in high yield a mineral acid salt of an amino acid methyl ester which contains a lesser amounts of impurities such as methanol, water and amino acid from the esterification of an amino acid with methanol in methanol in the presence of a mineral acid Mineral acid salts of the amino acid methyl esters are important as intermediates in the synthesis of peptides, for example, aspartame, a dipeptide sweetener, and medicines.

(ii) Description of the Prior Art

The esterification of amino acids is known from long ago and fundamentally the process developed by Curtius et al. is still used commercially even today. This process comprises first saturating, with hydrogen chloride, methanol in which an amino acid is dispersed and then, after the reaction is complete, removing excess methanol therefrom, adding fresh methanol thereto so as to increase the concentration of a reaction products, repeating these steps, afterward dehydrating the reaction solution, and finally crystallizing the product using ether or petroleum ether to obtain the desired product. However, this procedure has the deficiencies that in order to remove water formed during the reaction from the system, a great deal of the alcohol is consumed, and what is worse, hydrolysis proceeds in the course of the repeated concentration step. As a result, the yield of the esterified product which is obtained after filtration and drying is at most 90% or so. In addition, if the amino acid produced by the hydrolysis is present in a substantial amount in the thus-produced mineral acid salt, the separation of the desired product from the impurities becomes difficult.

Moreover, because the ether is difficult to handle and recover, its use for the crystallization in the above-described process is not industrially practical.

Another process is also known which comprises first heating an amino acid together with p-toluenesulfonic acid, ethanol and carbon tetrachloride, and then removing the thus-formed water as a azeotropic mixture from the system, whereby a product is obtained as a p-toluene sulfonate salt of an amino acid ethyl ester (Nikkashi, 83, p. 1151, 1962). However, in this process, a nonvolatile acid is required, which is not readily removed from the reaction product, and when methanol is used as the alcohol, a large amount of methanol is consumed, because methanol is removed together with carbon tetrachloride from the system as an azeotropic mixture. Thus, this process is also impractical from an industrial viewpoint.

In Japanese Patent Laid-open No. 165,560/1989, an esterification process is disclosed which comprises reacting an amino acid with an alcohol to prepare an amino acid ester, while the water formed during the reaction is distilled off with the alcohol out of the system. However, this process requires a large amount of the alcohol to remove the water, as in the abovementioned conventional technique, and it also has the drawback that its efficiency is very poor.

In these techniques, after esterification, the crystals can be deposited and separated by filtration, but the filter cake contains water formed during the reaction and a good deal of methanol. If the amino acid ester containing water and the alcohol is directly used as a reaction starting material, the results of reaction are often adversely affected. Therefore, it is an important task to remove the water and the alcohol from the amino acid ester before it is used as a starting material. However if an attempt is made to completely remove water and the alcohol from the reaction mixture by heating, a prolonged operation at a high temperature is required, which causes hydrolysis of the ester and racemization of the amino acid methyl ester occur. Consequently, it is required that the isolation/purification operation is carried out under moderate conditions, which leads to a poor efficiency and a low yield. For this reason, the above-mentioned conventional techniques are industrially unsatisfactory.

SUMMARY OF THE INVENTION

An object of the present invention is to provide an improved process for producing and efficiently isolating in high yield and purity a mineral acid salt of an amino acid methyl ester, from a reaction solution produced by the esterification of an amino acid with methanol in methanol in the presence of a mineral acid.

The present invention is an improved process for producing and isolating in high purity and in high yield a mineral acid salt of an amino acid methyl ester from a reaction solution produced by esterifying an amino acid with methanol in methanol in the presence of a mineral acid, which comprises the steps of (a) cooling the reaction solution obtained from the esterification reaction;

(b) separating the precipitated crystals from the supernatant liquid;

(c) removing methanol and water from the separated crystals, either by evaporation or washing with organic solvent; and (d) recycling the supernatant liquid or the solids in the supernatant liquid for reuse in the esterification reaction.

In the above-mentioned process, the wet crystals are dried at a low temperature or washed with another organic solvent, and therefore water and methanol present in the crystals can be removed therefrom without hydrolyzing the mineral salt of the amino acid methyl ester. On the other hand, since the supernatant liquid or the solids in the supernatant liquid is recycled, the loss of the amino acid starting material can be minimized, and the recovery of the mineral acid salt of the amino acid methyl ester from the reaction solution can be also increased, which can increase the overall yield of product.

DESCRIPTION OF THE PREFERRED EMBODIMENTS

The amino acid used in the present invention can be a natural or a non-natural material, and it can also be a racemate or an optically active material. Examples of such amino acid include neutral amino acids such as glycine, alanine, valine, leucine, isoleucine, phenylalanine, serine, threonine; basic amino acids such as lysine and arginine; acidic amino acids such as aspartic acid and glutamic acid; and derivatives thereof having such functional groups.

The mineral acid used in the present invention forms a salt with the amino group of the amino acid and functions as a catalyst for esterification. Examples of suitable mineral acids include hydrochloric acid, sulfuric acid, nitric acid and phosphoric acid. Hydrochloric acid is preferred, because it can easily be separated from the reaction solution after the esterification reaction.

The mineral acid is used in an at least equimolar amount with respect to the amino acid, generally from a small excess amount to about 5-fold moles. If the mineral acid is used excessively, the amount of the mineral acid which adheres to the obtained mineral salt of the amino acid methyl ester increases, so that a large amount of an alkali is required to neutralize the mineral acid.

The methanol for the esterification and as reaction solvent is preferably one-half to twice by the weight of the starting amino acid. If too much methanol is used, the yield of the precipitated mineral acid salt of the amino acid methyl ester decreases. Therefore, it is preferred that the lowest possible amount of methanol is used and the reaction is performed at the highest possible concentration. However, if the amount of methanol is too small, the slurry viscosity of the deposited crystals increases and the manual operations of stirring, pouring and the like become difficult.

The reaction system can be diluted by adding an inert organic solvent thereto. Examples of the suitable organic solvent include hydrocarbons such as toluene, xylene and hexane; ethers such as tetrahydrofuran and dioxane; aliphatic halogenated hydrocarbons such as methylene chloride,, ethylene chloride, trichloroethylene and tetrachloroethylene; aliphatic esters such as methyl acetate and methyl propionate; and phosphates such as trimethyl phosphate.

Other conditions for the esterification are not particularly restrictive, and conditions such as temperature, time and the like can be suitably decided considering whether or not the esterification of the used amino acid proceed readily. In general, a large excess of the mineral acid is used, and the reaction is performed by allowing the solution to stand for several days at room temperature. Alternatively, the solution is heated to a temperature in the vicinity of the reflux temperature of the methanol, and the reaction is then performed for several hours.

After the reaction, the solution is cooled to 20° C. or less, preferably 10° C. or less, so that the thus-produced mineral acid salt of the amino acid precipitates therefrom and the deposited salt is then separated in a conventional manner, e.g., by filtration, to obtain separated crystals, e.g., a filter cake to which only a small amount of water and methanol adhere.

The thus-isolated mineral acid salt of the amino acid methyl ester, e.g., in the form of a filter cake, is then preferably dried or washed with another organic solvent to remove the adhering methanol and water.

A drying operation is preferably carried out at the lowest possible temperature, because the mineral acid salt undergoes hydrolysis when exposed to a high temperature for a long time. In general, the filter cake is dried at a temperature of 20° to 80° C., preferably 60° C. or less. Preferably, the drying step is carried out under a reduced pressure, e.g., 100 mmHg or less.

Alternatively to remove methanol and water from the wet cake of the mineral acid salt of the amino acid methyl ester, the separated crystals are washed with an organic solvent.

Examples of the above-mentioned organic solvents which can be used include hydrocarbons, e.g., toluene, xylene and hexane; ethers, e.g., tetrahydrofuran and dioxane; aliphatic halogenated hydrocarbons, e.g., methylene chloride, ethylene chloride, trichloroethylene and tetrachloroethylene; aliphatic esters, e.g., ethyl acetate, methyl acetate, propyl acetate and methyl propionate; and phosphates, e.g., trimethyl phosphate and tri-n-butyl phosphate. However, if the solubility of the mineral acid salt of the amino acid methyl ester in the selected organic solvent is high, the yield of the product decreases as a result of the washing operation. For this reason, a solvent in which the mineral acid salt is substantially insoluble, e.g., hydrocarbons such as toluene, xylene and hexane is preferred. Toluene is particularly preferable.

The amount of the solvent, though not being particularly limited, is usually equal to or more in volume than that of the mineral acid salt wet cake of the amino acid methyl ester. Preferably the solvent is used to wash the crystals several times. The acceptable amount of methanol in the mineral acid salt of the amino acid methyl ester obtained by the above-mentioned procedure, depends upon the intended use of the amino acid methyl ester. If the weight amount of the methanol in the salt product is 5% or less of that of the mineral acid salt of the amino acid methyl ester, generally it presents no problem.

The resulting supernatant liquid from the separation step, e.g., the filtrate, can be recycled directly to the esterification reaction, after fresh methanol, mineral acid and the amino acid are added to the reaction vessel. If the supernatant liquid is recycled repeatedly, the water formed during the esterification will accumulate in the reaction solution. However, because a portion of the thus formed water adheres to the filter cake and is thus removed conveniently from the system, the amount of the water in the filtrate can be maintained at a predetermined level or less. The amount of the accumulated water thus depends upon the ratio of the amount of the water which adheres to the filter cake and is thereby removed from the system to the water which is recycled together with the supernatant (filtrate). Thus, when the reaction is performed at a high concentration, the amount of the supernatant to be recycled is decreased and the amount of the accumulated water is decreased.

As described above, the supernatant can be recycled, and the amount of the accumulated water in the reaction solution can be limited to a level of 20% by weight or less, preferably 10% by weight or less, whereby the efficiency of the esterification reaction is maintained highly.

Usually, however, it is preferable prior to recycling to concentrate the supernatant, e.g., to dryness, in order to remove at least some of the water therefrom. If the supernatant is concentrated at an elevated temperature, the amino acid methyl ester therein is hydrolyzed. However, this down not adversely affect the overall yield, because the supernatant is resubjected to the esterification conditions. The temperature for the concentration preferably is low enough that racemization of an optically active amino acid does not occur. Therefore, the concentration is preferably conducted at 20° to 60° C. under reduced pressure.

The present invention will now be described in detail with reference to the following examples.

EXAMPLE 1

To 165.2 g of methanol containing 79 g of hydrogen chloride was added 165.2 g of L-phenylalanine, and the solution was then stirred at 40° C. for 4 hours. High-speed liquid chromatography confirmed that the conversion into L-phenylalanine methyl ester was 99% or more.

After the reaction, the reaction solution was cooled to 3° C. followed by filtering in order to obtain 258.6 g of a filter cake. According to analysis, the water and methanol contents in this cake were 3.6% and 13.0%, respectively.

The filter cake was then dried by airflow at 50° C. for 10 hours to obtain 197.6 g of L-phenylalanine methyl ester hydrochloride having a purity of 96.8% and containing 0.2% of water and 1.2% of L-phenylalanine, in a yield of 88.7%.

The 150.8 g of thus-obtained filtrate was concentrated at 60° C. under a reduced pressure of 100 mmHg to obtain 43.9 g of a solid containing 19.8% of L-phenylalanine methyl ester hydrochloride, 23.3% of L-phenylalanine hydrochloride and 10.3% of water. This solid was then dissolved in 136.3 g of methanol, and 150.2 g of additional L-phenylalanine was added thereto. Afterward, the solution was allowed to absorb 79 g of a hydrochloric acid gas at 40° C. or less. After the esterification reaction was again performed at 40° C. for 4 hours, the reaction solution was cooled to 3° C. so as to deposit crystals of the mineral acid salt, which were collected by filtration. The resulting filter cake was then dried by airflow of 50° C. for 10 hours in order to obtain 199.5 g of L-phenylalanine methyl ester hydrochloride having a purity of 97.2% and containing 1.1% of L-phenylalanine and 0.1% of water. The yield of the product based on the newly added L-phenylalanine was 98.9%.

The filtrate containing 14.9 g (as phenylalanine) of phenylalanine methyl ester hydrochloride and phenylalanine hydrochloride was used again in an esterification of another batch of phenylalanine.

EXAMPLE 2

Following the same procedure as in Example 1, the esterification reaction was performed, followed by cooling in order to precipitate crystals of the mineral acid salt, which were collected by filtration and then dried to obtain 193.3 g (87.2% yield) of L-phenylalanine methyl ester hydrochloride having a purity of 97.3% and containing 0.1% of water and 1.1% of L-phenylalanine.

The 149.7 g of thus-obtained filtrate, containing 16.3% of L-phenylalanine methyl ester hydrochloride, 0.5% of L-phenylalanine and 4.4% of water, was directly used without concentrating, and 64.8 g of methanol and 145.8 g of additional L-phenylalanine were added thereto. The solution was then allowed to absorb 49.1 g of a hydrochloric acid at 40° C. or less. After the reaction mixture was maintained at 40° C. for 4 hours, the reaction solution was then cooled to 5° C. so as to deposit crystals of the hydrochloride and the latter were collected by filtration. The resulting filter cake was dried by airflow at 50° C. for 10 hours in order to obtain 190.1 g of L-phenylalanine methyl ester hydrochloride having a purity of 98.2% and containing 1.1% of L-phenylalanine and 0.1% of water. The yield of the product based on the newly added L-phenylalanine was 98.1%.

The thus-obtained filtrate was directly recycled five times without concentrating, and at this point in time, 8.3% of water was present in the reaction solution of the last batch. When the esterification reaction was over, a reaction ratio was 97%. After cooling, filtration and drying, crystals of the hydrochloride salt having a purity of 96.3% and containing 2.3% of L-phenylalanine and 0.1% of water were obtained in an overall yield, based on the total additional L-phenylalanine which was added while the reaction was performed six times, of 97.1%.

COMPARATIVE EXAMPLE 1

The same esterification reaction as in Example 1 was performed. Afterward, the methanol was concentrated at a temperature of 50° C. under reduced pressure, and the procedure of adding 200 g of methanol and concentrating was repeated twice. Ethyl ether was then added to the resulting oily residue, followed by crystallization, filtration and drying to obtain 211.1 g (91.3% yield) of L-phenylalanine methyl ester hydrochloride having a purity of 9.3% and containing 0.3% of water and 5.1% of L-phenylalanine.

EXAMPLE 3

The same esterification procedure as in Example 1 was followed, with the exception that the L-phenylalanine was replaced with 89.1 g of L-alanine and that 89.1 g of methanol and 42.6 g of hydrochloric acid were used. After cooling in order to deposit crystals of the hydrochloride salt, the latter were collected by filtration and then dried to obtain 120.5 g (84.3% yield) of L-alanine methyl ester hydrochloride having a purity of 97.7% and containing 0.1% of water and 1.2% of L-alanine.

The 70.2 g of resulting filtrate was concentrated at 60° C. under a reduced pressure of 100 mmHg to obtain 30.3 g of a solid containing 26.5% of L-alanine methyl ester hydrochloride, 30.5% of L-alanine hydrochloride and 8.5% of water. This solid was then dissolved in 71.0 g of methanol, and 76.5 g of additional L-alanine was added thereto. Afterward, the solution was allowed to absorb 42.6 g of a hydrochloric acid gas at 40° C. or less. After reaction mixture was maintained at 40° C. for 4 hours, the reaction solution was then cooled to 3° C. so as to deposit crystals of the hydrochloride salt, which were collected by filtration. The resulting filter cake was then dried by airflow at 50° C. for 10 hours to obtain 120.4 g of L-alanine methyl ester hydrochloride having a purity of 98.7% and containing 0.9% of L-alanine and 0.1% of water. The yield of product based on the additional L-alanine was 99.1%.

The filtrate, containing 12.2 g (as alanine) of alanine methyl ester hydrochloride and alanine hydrochloride, was used again in the esterification reaction.

EXAMPLE 4

The same esterification procedure as in Example 1 was followed with the exception that the L-phenylalanine was replaced with 133.1 g of L-aspartic acid and that 133.1 g of methanol and 64 g of hydrochloric acid were used. Following cooling to deposit the crystals, the latter were collected by filtration and then dried to obtain 160.5 g (78.4 yield) of L-aspartic acid dimethyl ester hydrochloride having a purity of 96.5% and containing 0.2% of water and 2.6% of the total of L-aspartic acid and α- and β-monomethyl esters of L-aspartic acid.

The 116.2 g of the thus-obtained filtrate was concentrated at 60° C. under a reduced pressure of 100 mmHg to obtain 61.1 g of a solid containing 5.6% of L-aspartic acid dimethyl ester hydrochloride, 55.2% of L-aspartic acid hydrochloride and 6.4% of water. This solid was then dissolved in 100.7 g of methanol, and 104.4 g of L-aspartic acid was newly added thereto. Afterward, the solution was allowed to absorb 64 g of a hydrochloric acid gas at 40° C. or less. After the reaction mixture was maintained at 40° C. for 4 hours, the reaction solution was then cooled to 3° C. so as to deposit the crystals, which were then collected by filtration. The resulting filter cake was then dried by airflow at 50° C. for 10 hours to obtain 156.4 g of L-aspartic acid dimethyl ester hydrochloride having a purity of 97.1% and containing 2.8% of the total of L-aspartic acid and α- and β-monomethyl esters of L-aspartic acid and 0.2% of water. The yield of the product, based on the additional L-aspartic acid was 98.0%.

The filtrate, containing 18.6 g (as aspartic acid) of aspartic acid dimethyl ester hydrochloride and aspartic acid hydrochloride, was used again in the esterification reaction.

EXAMPLE 5

The same esterification procedure as in Example 1 was followed with the exception that the L-phenylalanine was replaced with 105.6 g of L-serine and that 105.6 g of methanol and 50.5 g of hydrochloric acid were used. Following cooling to deposit the crystals, which were collected by filtration and then dried to obtain 134.4 g (83.8% yield) of L-serine methyl ester hydrochloride having a purity of 97.0% and containing 0.2% of water and 0.7% of L-serine.

The 84.9 g of the thus-obtained filtrate was concentrated at 60° C. under a reduced pressure of 100 mmHg in order to obtain 43.9 g of a solid containing 12.1% of L-serine methyl ester hydrochloride, 39.5% of L-serine hydrochloride and 12.8% of water. This solid was then dissolved in 78.2 g of methanol, and 89.1 of additional L-serine was added thereto. Afterward, the solution was allowed to absorb 50.5 g of a hydrochloric acid gas at 40° C. or less. After the reaction mixture was maintained at 40° C. for 4 hours, the reaction solution was then cooled to 3° C. so as to deposit the crystals, which were collected by filtration. The resulting filter cake was then dried by airflow at 50° C. for 10 hours to obtain 133.6 g of L-serine methyl ester hydrochloride having a purity of 97.2% and containing 0.9% of L-serine and 0.1% of water. The yield of product, based on the additional L-serine, was 98.4%.

The filtrate, containing 16.2 g (as serine) of serine methyl ester hydrochloride and serine hydrochloride, was used again in the esterification reaction.

EXAMPLE 6

The same esterification procedure as in Example 1 was followed with the exception that the L-phenylalanine was replaced with 182.6 g of L-lysine hydrochloride and that 182.6 g of methanol and 87.3 g of hydrochloric acid were used. Following cooling in order to deposit the crystals, the latter were collected by filtration and then dried to obtain 196.2 g (81.3% yield) of L-lysine methyl ester dihydrochloride having a purity of 96.6% and containing 0.2% of water and 1.3% of L-lysine hydrochloride.

The 190.9 g of thus-obtained filtrate was concentrated at 60° C. under a reduced pressure of 100 mmHg in order to obtain 52.0 g of a solid containing 23.3% of L-lysine methyl ester dihydrochloride, 51.0% of L-lysine dihydrochloride and 12.3% of water. This solid was then dissolved in 162.2 g of methanol, and 151.0 g of additional L-lysine hydrochloride was added thereto. Afterward, the solution was allowed to absorb 87.3 g of a hydrochloric acid gas at 40° C. or less. After the reaction mixture was maintained at 40° C. for 4 hours, the reaction solution was then cooled to 3° C. so as to deposit crystals, which were collected by filtration. The resulting filter cake was then dried by airflow at 50° C. for 10 hours to obtain 197.0 g of L-lysine methyl ester dihydrochloride having a purity of 96.3% and containing 1.5% of L-lysine hydrochloride and 0.2% of water. The yield of the product based on the additional L-lysine hydrochloride was 98.4%.

The filtrate, containing 31.0 g (as lysine) of lysine methyl ester hydrochloride and lysine hydrochloride, was used again in the esterification reaction.

EXAMPLE 7

The same esterification procedure as in Example 1 was followed with the exception that 165.2 g of L-phenylalanine and 165.2 g of methanol were used and that the hydrochloric acid was replaced with 120.1 g of 98% sulfuric acid. The reaction was conducted at 60° C. for 8 hours, followed by cooling in order to deposit the crystals, which were collected by filtration and then dried to obtain 184.9 g (63.8% yield) of L-phenylalanine methyl ester sulfate having a purity of 95.7% and containing 0.3% of water and 2.4% of L-phenylalanine.

The 200.7 g of thus-obtained filtrate was concentrated at 50° C. under a reduced pressure of 100 mmHg in order to obtain 120.3 g of a solid containing 24.0% of L-phenylalanine methyl ester sulfate, 50.5% of L-phenylalanine sulfate and 16.5% of water. This solid was then dissolved in 153.7 g of methanol, and 109.9 g of additional L-phenylalanine and 66.6 g of 98% sulfuric acid were added thereto. After the reaction mixture was maintained at 60° C. for 8 hours, the reaction solution was then cooled to 3° C. so as to deposit the crystals, which were collected by filtration. The resulting filter cake was then dried by airflow at 50° C. for 10 hours to obtain 181.9 g of L-phenylalanine methyl ester sulfate having a purity of 95.4% and containing 3.0% of L-phenylalanine and 0.2% of water. The yield of the product based on the additional L-phenylalanine was 94.1%.

The filtrate, containing 56.3 g (as phenylalanine) of phenylalanine methyl ester sulfate and phenylalanine sulfate, was used again in the esterification reaction.

EXAMPLE 8

The same esterification procedure as in Example 1 was followed with the exception that 165.2 g of L-phenylalanine and 165.2 g of methanol were used and that hydrochloric acid was replaced with 132.1 g of 89% phosphoric acid. The reaction was conducted at 60° C. for 8 hours, followed by cooling in order to deposit the crystals, which were collected by filtration and then dried to obtain 169.4 g (58.1% yield) of L-phenylalanine methyl ester phosphate having a purity of 95.1% and containing 0.3% of water and 3.0% of L-phenylalanine.

The 227.2 g of thus-obtained filtrate was concentrated at 60° C. under a reduced pressure of 100 mmHg in order to obtain 138.9 g of a solid containing 18.8% of L-phenylalanine methyl ester phosphate, 55.7% of L-phenylalanine phosphate and 16.3% of water. This solid was then dissolved in 155.1 g of methanol, and 101.1 g of additional L-phenylalanine and 67.4 g of 89% phosphoric acid were added thereto. After the reaction mixture was maintained at 60° C. for 8 hours, the reaction solution was then cooled to 3° C. so as to deposit the crystals, which were collected by filtration. The resulting filter cake was then dried by airflow at 50° C. for 10 hours to obtain 169.8 g of L-phenylalanine methyl ester phosphate having a purity of 95.1% and containing 3.2% of L-phenylalanine and 0.2% of water. The yield of the product, based on the additional L-phenylalanine, was 95.2%.

The filtrate, containing 63.6 g (as phenylalanine) of phenylalanine methyl ester phosphate and phenylalanine phosphate, was used again in the esterification reaction.

EXAMPLE 9

To 165.2 g of methanol containing 98 g of hydrogen chloride was added 165.2 g of L-phenylalanine, and the solution was then stirred at 40° C. for 4 hours. High-speed liquid chromatography confirmed that the conversion into L-phenylalanine methyl ester was 99% or more.

After the reaction, the reaction solution was cooled to 3° C., followed by filtering in order to obtain 252.4 g of a filter cake. According to analysis, the water and methanol contents thereof were 3.5% and 13.8%, respectively.

This filter cake was then redispersed in 200 g of toluene and the dispersion was stirred for 30 minutes and then filtered and air dried, thereby obtaining 215.6 g of L-phenylalanine methyl ester hydrochloride as a cake. Analysis confirmed that the cake had a purity of 88.7% and contained 2.2% of L-phenylalanine, 2.6% of water and 4.2% of methanol. Yield was 88.7%.

The filtrate was directly used to another batch of the same esterification reaction as shown in Example 2.

EXAMPLE 10

To a mixed solvent of 165.2 g of methanol containing 98 g of hydrogen chloride and 80 g of toluene was added 165.2 g of L-phenylalanine, and the solution was then stirred at 40° C. for 4 hours. Analysis of the resulting reaction solution by means of high-speed liquid chromatography confirmed that conversion into L-phenylalanine methyl ester hydrochloride was 99% or more.

After the reaction, the reaction solution was cooled to 3° C. The crystal-containing cooled solution, which had separated into two layers, was then filtered as such to thereby obtain 223.7 g of a filter cake. According to analysis, water and methanol contents thereof were 2.3% and 5.9%, respectively.

This filter cake was then redispersed in 200 g of toluene, and the dispersion was stirred for 30 minutes and then filtered to obtain 213.4 g (86.5% yield) of L-phenylalanine methyl ester as a cake which, by analysis, had a purity of 87.4% and contained 2.4% of L-phenylalanine, 1.9% of water and 2.3% of methanol.

The filtrate was directly used to another batch of the same esterification reaction as shown in Example 2.

What is claimed is:

1. A cyclical process for producing and isolating in high purity and in high yield a mineral acid salt of an amino acid methyl ester from a reaction solution produced by esterifying an amino acid, in the presence of a mineral acid, with methanol in methanol with the total amount of methanol being 0.5-2 times the weight of the amino acid, which comprises the steps of:
   (a) precipitating the esterified amino acid from the reaction solution obtained from the esterification reaction by cooling without additional of additional methanol;
   (b) separating the precipitated crystals form the supernatant liquid at a water concentration in the supernatant of less than 20% by weight;
   (c) removing methanol and water from the separated crystals, either by evaporation or washing with organic solvent; and
   (d) recycling the supernatant liquid or only the solids in the supernatant liquid, after separation of the solids therefrom, for reuse in the esterification reaction.

2. A process according to claim 1 wherein the methanol is removed from the separated crystals by drying at a temperature of 60° C. or less.

3. A process according to claim 1 wherein the methanol is removed from the separated crystals by washing with solvent.

4. A process according to claim 3, wherein the solvent is toluene.

5. A process according to claim 1 wherein the precipitated crystals are removed from the supernatant liquid by filtration.

6. A process according to claim 1 wherein the supernatant liquid is concentrated to dryness prior to the solids therein being recycled for reuse in the esterification reaction.

7. A process according to claim 1 wherein the mineral acid is hydrogen chloride.

8. A process according to claim 1 wherein the amino acid is a neutral amino acid.

9. A process according to claim 1 wherein the amino acid is L-phenylalanine.

10. A process according to claim 1, wherein the methanol is removed from the separated crystals by drying at a temperature of 60° C. or less, wherein the precipitated crystals are removed from the supernatant liquid by filtration, wherein the supernatant liquid is recycled for reuse in the esterification reaction, wherein the mineral acid is hydrogen chloride and wherein the amino acid is a neutral amino acid.

11. A process according to claim 10, wherein the amino acid is L-phenylalanine, and wherein the esterification reaction is conducted a multiplicity of times and the supernatant liquid is recycled and used as a reaction solvent for the esterification a multiplicity of times.

12. A process according to claim 1, wherein the methanol is removed from the separated crystals by drying at a temperature of 60° C. or less, wherein the precipitated crystals are removed from the supernatant liquid by filtration, wherein the supernatant liquid is concentrated to dryness prior to the solids therein being recycled for reuse in the esterification reaction, wherein the mineral acid is hydrogen chloride and the amino acid is a neutral amino acid.

13. A process according to claim 12, wherein the amino acid is L-phenylalanine, and wherein the esterification reaction is conducted a multiplicity of times and the solids separated from the cooled supernatant liquid is recycled and used in the esterification a multiplicity of times.

* * * * *